United States Patent [19]

Mehta et al.

[11] Patent Number: 5,464,622
[45] Date of Patent: Nov. 7, 1995

[54] ANTIMICROBIAL COMPOSITIONS COMPRISING IODOPROPARGYL BUTYLCARBAMATE AND 2-MERCAPTOPYRIDINE N-OXIDE AND METHOD OF CONTROLLING MICROBES

[75] Inventors: Raj I. Mehta, Gujarat, Ind.; Barry C. Lange, Lansdale, Pa.; Samuel E. Sherba, Willingboro, N.J.

[73] Assignee: Rohm and Haas Company, Philadelphia, Pa.

[21] Appl. No.: 971,694

[22] Filed: Nov. 4, 1992

Related U.S. Application Data

[63] Continuation of Ser. No. 619,281, Nov. 27, 1990, abandoned.

[51] Int. Cl.[6] .................. A01N 31/08; A01N 31/16; A01N 47/10; A01N 25/00
[52] U.S. Cl. .................. 424/405; 424/76.8; 424/401; 504/150; 514/345; 514/348; 546/290; 546/292; 546/294
[58] Field of Search .................. 424/401, 76.8, 424/405; 546/290, 292, 294; 514/345; 504/150

[56] References Cited

U.S. PATENT DOCUMENTS

| 3,281,366 | 10/1966 | Judge et al. | 252/107 |
|---|---|---|---|
| 3,726,970 | 4/1973 | Weisse | 424/656 |
| 4,250,046 | 2/1981 | Przybylinski | 252/49.3 |
| 4,552,885 | 11/1985 | Gabriele et al. | 514/316 |
| 4,632,991 | 12/1986 | Maurer et al. | 546/6 |
| 4,659,830 | 4/1987 | Maurer et al. | 546/6 |
| 4,806,263 | 2/1989 | Leathers et al. | 252/106 |
| 4,818,436 | 4/1989 | French et al. | 252/400.23 |
| 4,844,891 | 7/1989 | Rosen et al. | 424/76.4 |
| 4,883,659 | 11/1989 | Goodman et al. | 424/78.03 |
| 4,925,582 | 5/1990 | Bennett | 252/49.3 |
| 4,950,685 | 8/1990 | Ward | 514/479 |
| 4,977,186 | 12/1990 | Gruening | 514/479 |
| 5,162,343 | 11/1992 | Whitekettle et al. | 514/345 |

OTHER PUBLICATIONS

CA92(3):17148b, Rossmoore et al. "Utility of Biocide . . . Fluids.", Lubric. Eng. 35(10), pp. 559–563.
CA91(16):127567z, Izzat et al., Potent. of Antimicrob. Act. of Cutting Fluid Preserv. by Edta. Lubric. Eng. 35(3), pp. 153–159.
CA92(3):17148b, Rossmoore et al., Utility of Biocide Comb. in Controlling Miked Microbial Populations in Metal Working Fluids., Lubric. Eng. 35(10), pp. 559–563.
S. D. Strauss, et al., J. Power, S1, Jun. 1984. Kull et al., Applied Microbiology, 9,538 (1961).
Kull et al., Applied Microbiology, 9,538 (1961).

Primary Examiner—John C. Bleutge
Assistant Examiner—Robert H. Harrison
Attorney, Agent, or Firm—Michael B. Fein

[57] ABSTRACT

A synergistic antimicrobial composition comprising 2-mercaptopyridine N-oxide, and salts thereof, and iodopropargyl butylcarbamate in a ratio to each other which exhibits synergism is disclosed.

2 Claims, No Drawings

ANTIMICROBIAL COMPOSITIONS COMPRISING IODOPROPARGYL BUTYLCARBAMATE AND 2-MERCAPTOPYRIDINE N-OXIDE AND METHOD OF CONTROLLING MICROBES

This application is a continuation of application Ser. No. 619,281, filed Nov. 27, 1990 now abandoned.

BACKGROUND OF THE INVENTION

1. Field of the Invention

The present invention relates to antimicrobial compositions and methods of controlling microbes.

2. Description of the Prior Art

The presence of microbes in various aqueous systems such as latices, paints, coatings, cooling water systems, decorative ponds and the like, can cause deterioration or disfigurement of these systems. For example, painted surfaces may be disfigured by the unsightly buildup of microbes, thus detracting from the overall aesthetics of the painted article; cooling towers may lose efficiency due to the buildup of microbes on surfaces, thus reducing the heat transfer capabilities of the tower. It is conventional to practice methods which inhibit the microbial deterioration of such systems by incorporating a variety of additives or combination of additives that are characterized by having antimicrobial activity.

A wide variety of materials have been used to control microbes in different environments, some of which are: chlorine/bromine compounds, glutaraldehyde, isothiazolones, organotin formulations, copper salts, quaternary ammonium compounds (SD Strauss and PR Puckorius in *J. Power*, S1, June 1984), and triazines. Each has deficiencies related to toxicity, pH and temperature sensitivity, limited effectiveness, chemical stability, and/or compatibility.

Based on the aforementioned performance deficiencies of conventional antimicrobial compounds there is a need for more effective antimicrobial agents that can be used at lower dosage rates, thus being more cost effective for the end user, reducing the pollution load on the affected environmental systems, and reducing the side effects to nearby non-target organisms, such as fish, useful crops, etc.

Among the many antimicrobial compounds which have been proposed, only a relatively small number have become useful in practice among which are iodopropargyl butylcarbamate and 2-mercaptopyridine n-oxide. However, as far as we know, no one has ever proposed using these two antimicrobials together.

SUMMARY OF THE INVENTION

It is the object of this invention to provide a method of controlling microbes at very low levels of active ingredient. It is a further object to use compositions which are compatible with a variety of systems susceptible to deterioration by microbes. Another object is to provide a method of controlling microbes in cooling towers, paints, marine antifoulant coatings, spray washes, swimming pools, coatings, decorative ponds, fabric, leather, paper, wood, metal working fluids, cosmetic formulations, fuel systems, therapeutic pharmaceutical formulations, and the like, without objectionable by-product odors, discoloration, or otherwise detrimental effects on the treated (and controlled) systems. These objects, and others which will become apparent from the following disclosure, are achieved by the present invention which, in one aspect comprises a composition useful for controlling microbes comprising (A) a compound (metal salt of 2-mercaptopyridine N-oxide) of the formula

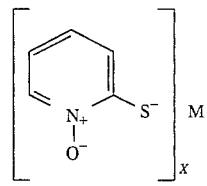

wherein M is a metal cation selected from the group consisting of sodium, potassium, calcium, magnesium and zinc; and where X=1 when M is sodium or potassium and X=2 when M is magnesium, calcium or zinc;

and (B) a compound (iodopropargyl butylcarbamate) of the formula

in a ratio to each other which exhibits synergism.

In another aspect, the invention comprises a method for inhibiting the growth of a member selected from the group consisting of bacteria, fungi, algae and mixtures thereof in a locus subject to contamination by said member, which comprises incorporating onto or into the locus, in an amount which is effective to adversely affect the growth of said member, the aforementioned composition.

Another aspect of the invention is a method of controlling microbes in cooling tower water comprising maintaining a concentration of the aforementioned composition in the water.

The invention also comprises microbe-resistant coating or impregnant compositions and marine antifoulant compositions comprising the antimicrobial composition.

In a preferred aspect of the invention the antimicrobial composition is incorporated into therapeutic pharmaceutical formulations, e.g., topical antifungal treatments such as shampoos, creams and ointments.

DETAILED DESCRIPTION OF THE INVENTION AND THE PREFERRED EMBODIMENTS

We have discovered an especially effective composition useful for controlling microbes comprising (A) a compound (metal salt of 2-mercaptopyridine N-oxide) of the formula

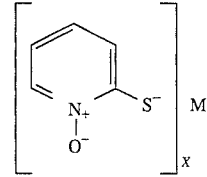

wherein M is a metal cation selected from the group consisting of sodium, potassium, calcium, magnesium and zinc; and where X=1 when M is sodium or potassium and X=2 when M is magnesium, calcium or zinc;

and (B) a compound (iodopropargyl butylcarbamate) of the formula

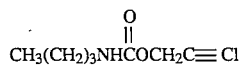

in a ratio to each other which exhibits synergism.

In accordance with the invention a method of controlling microbes comprises using an effective amount of the aforementioned composition.

Another important utility is in imparting microbial resistance to a coating or an impregnant composition comprising incorporation of the composition of the invention in the coating or impregnant, preferably at a concentration of about 0.1 ppm to about 2 percent, more preferably at a concentration of about 1 ppm to 1 percent, and most preferably at a concentration of about 10 to 4000 ppm.

In a marine antifoulant composition, on the other hand, the antimicrobial composition of the invention comprises about 1 to 10 percent of the antifoulant composition.

In a therapeutic pharmaceutical formulation, e.g., lotion, cream, ointment or topical treatment; in the treatment of metal working fluids; and in the protection of fabric, leather, paper or wood materials, the microbicidal composition is added at a concentration of from about 0.1 ppm to about 2 percent by weight. In aqueous media, the microbicidal composition comprises from about 0.1 ppm to about 1 percent of the aqueous system depending on the specific end use; for example, in cooling water tower applications and with pulp or paper manufacturing processes, the microbicidal composition is added at a concentration from about 0.1 to about 1000 ppm by weight. In cosmetic formulations, e.g., face or hand creams, toiletries, etc.; and in the treatment of fuel systems, e.g., jet fuel, gasoline, heating oil, etc., the microbicidal composition is added at a concentration of from about 0.1 ppm to about 1 percent by weight.

The microbial resistant compositions can also be used in construction products such as stucco, roof mastics, wall mastics, and masonry coatings for algae protection; in clear finishes and coatings to protect underlying substrates from algae; for algae control in aquaculture, including aquaria, fish hatcheries, shrimp ponds, finfish ponds, mollusc and crustacean cultivation; for algae control in recreational and decorative bodies of water such as swimming pools, lakes, fountains and decorative ponds; for algae control in bodies of water for industrial or municipal use, such as settling or separation ponds, waste treatment ponds, and water reservoirs; for algae control in hydroponic farming; for algae control in processing and manufacture of pulp and paper products; for inclusion in plastics or in coatings for plastics to protect against algae; and in plastics or coatings for plastics for swimming pool liners., We prefer compositions wherein the weight ratio of (A) to (B) is about 0.1:100 to about 100:0.1. A particularly preferred ratio range is about 200:1 to about 1:99 by weight.

The following examples represent just a few of the many uses of the invention. They are intended to be illustrative but not limiting. Various modifications, alternatives, and improvements should become apparent to those skilled in the art without departing from the spirit and scope of the invention.

EXAMPLES

A. General Procedure

MIC values represent the Minimum Inhibitory Concentration. This is defined as the lowest level of compound required to completely inhibit (repress) the growth of a given organism.

A synergistic effect is defined as the response of two variables which is greater than the sum of both parts alone. Synergy was determined from combination studies with two compounds by the method of calculation described by F. C. Kull, P. C. Eisman, H. D. Sylwestrowicz and R. K. Mayer, *Applied Microbiology* 9,538 (1961):

$$\frac{Q_a}{Q_A} + \frac{Q_b}{Q_B} = \text{synergism index} \quad (SI)$$

where:
$Q_A$=quantity of compound A, acting alone, producing an end point (MIC)
$Q_a$=quantity of compound A, in mixture, producing an end point (MIC)
$Q_B$=quantity of compound B, acting alone, producing an end point (MIC)
$Q_b$=quantity of compound B, in mixture, producing an end point (MIC)

The following SI values may be attained:
SI>1 represents antagonistic effect,
SI=1 represents additive effect,
SI<1 represents synergy.

Efficacy studies were conducted on a variety of microorganisms with iodopropargyl butylcarbamate and 2-mercaptopyridine N-oxide metal salt mixtures. The MIC studies were conducted using microtiter plate assays in trypticase soy broth (TSB) medium. In this method, a wide range of concentrations was tested by preparing two-fold serial dilutions of the compound in 96-well plastic microtiter plates. All liquid media transfers were performed with calibrated single or multichannel digital pipetters. Stock solutions of compounds were prepared in appropriate solvents and dispensed to the growth medium. All subsequent dilutions in plates were made using the desired growth medium; total volume of liquid in each well was 100 μl. Each plate contained a concentration of both compounds made by serially titrating equal volumes of liquids in two directions in the microtiter plate. Each plate contained a control row for each combination (one component only), hence, the individual compound MIC values were also determined.

EXAMPLE 1

*Pseudomonas aeruginosa*

Using a pure culture of *Pseudomonas aeruginosa*, various combinations of iodopropargyl butylcarbamate (Compound B, acetone solution) and 2-mercaptopyridine N-oxide sodium salt (Compound A) were subjected to MTC determinations (TSB medium):

| MIC Data on Compound A/Compound B Combinations (ppm) | | | |
|---|---|---|---|
| $Q_a$ | $Q_b$ | $Q_a/Q_b$ | SI |
| 25($Q_A$) | 0 | — | 1.0 |
| 12.5 | 31 | 29/71 | 0.63 |
| 12.5 | 63 | 17/83 | 0.75 |
| 6.3 | 125 | 5/95 | 0.75 |
| 3.1 | 125 | 2/98 | 0.63 |
| 0 | 250($Q_B$) | — | 1.0 |

The block diagram illustrates the experimental protocol used to establish the synergy relationship for Compound A/Compound B combinations against *Pseudomonas aeruginosa*: X=growth of organism, blanks=no growth of organism.

|   | 1 | 2 | 3 | 4 | 5 | 6 | 7 | 8 | 9 | 10 | 11 | 12 |   |
|---|---|---|---|---|---|---|---|---|---|----|----|----|---|
| A |   |   |   |   |   |   |   |   |   |    |    |    | 250 ppm |
| B |   |   |   |   | X | X | X | X | X | X  | X  | X  |   |
| C |   |   | X | X | X | X | X | X | X | X  | X  | X  |   |
| D |   |   | X | X | X | X | X | X | X | X  | X  | X  | Compound B |
| E |   | X | X | X | X | X | X | X | X | X  | X  | X  |   |
| F |   | X | X | X | X | X | X | X | X | X  | X  | X  |   |
| G |   | X | X | X | X | X | X | X | X | X  | X  | X  |   |
| H |   | X | X | X | X | X | X | X | X | X  | X  | X  | 0 ppm |
|   | 25 ppm |   |   |   |   | Compound A |   |   |   |    |    | 0 ppm |   |

EXAMPLE 2

*Aspergillus niger*

In a manner similar to Example 1 another MIC study was conducted with iodopropargyl butylcarbamate (Compound B, acetone stock solution) and 2-mercaptopyridine N-oxide sodium salt (Compound A) against *Aspergillus niger*.

| MIC Data on Compound A/Compound B Combinations (ppm) | | | |
|---|---|---|---|
| $Q_a$ | $Q_b$ | $Q_a/Q_b$ | SI |
| 25($Q_A$) | 0 | — | 1.0 |
| 12.5 | 0.08 | 160/1 | 0.63 |
| 12.5 | 0.16 | 99/1 | 0.75 |
| 6.3 | 0.16 | 97/3 | 0.50 |
| 6.3 | 0.31 | 95/5 | 0.75 |
| 3.1 | 0.16 | 95/5 | 0.38 |
| 3.1 | 0.31 | 91/9 | 0.63 |
| 1.6 | 0.16 | 91/9 | 0.31 |
| 1.6 | 0.31 | 83/17 | 0.56 |
| 0.8 | 0.16 | 83/17 | 0.28 |
| 0.8 | 0.31 | 71/29 | 0.53 |
| 0.4 | 0.16 | 71/29 | 0.27 |
| 0.4 | 0.31 | 56/44 | 0.52 |
| 0.2 | 0.31 | 38/62 | 0.51 |
| 0.1 | 0.31 | 24/76 | 0.50 |
| 0 | 0.63($Q_B$) | — | 1.0 |

The block diagram illustrates the experimental protocol used to establish the synergy relationship for Compound A/Compound B combinations against *Aspergillus niger*: X=growth of organism, blanks=no growth of organism.

|   | 1 | 2 | 3 | 4 | 5 | 6 | 7 | 8 | 9 | 10 | 11 | 12 |   |
|---|---|---|---|---|---|---|---|---|---|----|----|----|---|
| A |   |   |   |   |   |   |   |   |   |    |    |    | 5 ppm |
| B |   |   |   |   |   |   |   |   |   |    |    |    |   |
| C |   |   |   |   |   |   |   |   |   |    |    |    |   |
| D |   |   |   |   |   |   |   |   |   |    |    |    | Compound B |
| E |   |   |   |   |   |   |   |   |   |    | X  |    |   |
| F |   |   |   |   |   |   |   |   |   | X  | X  | X  |   |
| G |   |   |   | X | X | X | X | X | X | X  | X  |    |   |
| H |   |   | X | X | X | X | X | X | X | X  | X  | X  | 0 (ppm) |
|   | 100 ppm |   |   |   |   | Compound A |   |   |   |    | 0 (ppm) |   |   |

What is claimed is:

1. A microbicidal composition comprising a synergistic mixture a first component of which is a sodium salt of 2-mercaptopyridine N-oxide of the formula

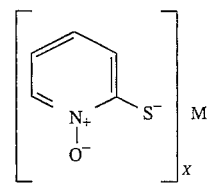

wherein M is sodium; where X=1; and a second component of which is iodopropargyl butylcarbamate wherein the ratio of the first component to the second component is in the range from about 200/1 to about 1/99.

2. A coating or impregnant composition comprising from about 0.1 ppm to about 2 percent by weight of the composition of claim 1.

\* \* \* \* \*